(12) United States Patent
Prevoo et al.

(10) Patent No.: US 12,171,494 B2
(45) Date of Patent: Dec. 24, 2024

(54) METHOD OF PERFORMING AN EYE EXAMINATION TEST FOR EXAMINING EYES OF A USER AS WELL AS A CORRESPONDING COMPUTING DEVICE

(71) Applicant: Easee Health B.V., Amsterdam (NL)

(72) Inventors: Yves Franco Diano Maria Prevoo, Amsterdam (NL); Francesco Cassano, Amsterdam (NL); Jouke Waleson, Utrecht (NL)

(73) Assignee: EASEE HEALTH B.V., Amsterdam (NL)

( * ) Notice: Subject to any disclaimer, the term of this patent is extended or adjusted under 35 U.S.C. 154(b) by 679 days.

(21) Appl. No.: 17/310,613

(22) PCT Filed: Feb. 17, 2020

(86) PCT No.: PCT/NL2020/050089
§ 371 (c)(1),
(2) Date: Aug. 13, 2021

(87) PCT Pub. No.: WO2020/171696
PCT Pub. Date: Aug. 27, 2020

(65) Prior Publication Data
US 2022/0142474 A1    May 12, 2022

(30) Foreign Application Priority Data
Feb. 19, 2019  (NL) ...................................... 2022598

(51) Int. Cl.
*A61B 3/14*    (2006.01)
*A61B 3/00*    (2006.01)
(Continued)

(52) U.S. Cl.
CPC .............. *A61B 3/14* (2013.01); *A61B 3/0008* (2013.01); *A61B 3/0041* (2013.01);
(Continued)

(58) Field of Classification Search
CPC ....... A61B 3/14; A61B 3/0008; A61B 3/0041; A61B 5/7405; A61B 3/032; G06T 7/0012;
(Continued)

(56) References Cited

U.S. PATENT DOCUMENTS 11,335,028 B2 *   5/2022   Bai ........................... G06T 7/55
2008/0292151 A1   11/2008  Kurtz
(Continued)

OTHER PUBLICATIONS

International Search Report in International Patent Application No. PCT/NL2020/050089, mailed Jul. 28, 2020 (3 pages).

*Primary Examiner* — Tuyen Tra
(74) *Attorney, Agent, or Firm* — Nixon Peabody LLP

(57) ABSTRACT

A method of performing an eye examination test for examining eyes of a user, said method using a computing device, said computing device comprising an image capturing unit arranged for capturing images, said method comprising the steps of capturing, by said capturing unit, an image of said user and its surroundings, dividing, by said computing device, said captured image into a plurality of bins, estimating, by said computing device, light intensity of each of said plurality bins, determining, by said computing device, an area of anomalous light intensity in said captured image based on said step of estimation wherein said estimated light intensity is above a predetermined threshold value, performing, by said computing device, said eye examination test, taking said determined area of anomalous light into account.

14 Claims, 3 Drawing Sheets

(51) Int. Cl.
*A61B 5/00* (2006.01)
*G06T 7/00* (2017.01)
*G06T 7/70* (2017.01)
*H04N 23/71* (2023.01)

(52) U.S. Cl.
CPC .......... *A61B 5/7405* (2013.01); *G06T 7/0012* (2013.01); *G06T 7/70* (2017.01); *H04N 23/71* (2023.01); *G06T 2207/30041* (2013.01); *G06T 2207/30168* (2013.01)

(58) Field of Classification Search
CPC ............. G06T 7/70; G06T 2207/30041; G06T 2207/30168; H04N 23/71
See application file for complete search history.

(56) References Cited

U.S. PATENT DOCUMENTS

| | | |
|---|---|---|
| 2011/0157550 A1 | 6/2011 | Chen |
| 2011/0187997 A1 | 8/2011 | Tanassi |
| 2013/0128229 A1 | 5/2013 | Huang |
| 2016/0232408 A1 | 8/2016 | Lee |
| 2016/0266643 A1 | 9/2016 | Martensson |
| 2018/0136486 A1 | 5/2018 | MacNamara |
| 2019/0012784 A1 | 1/2019 | Wiley |

* cited by examiner

METHOD OF PERFORMING AN EYE EXAMINATION TEST FOR EXAMINING EYES OF A USER AS WELL AS A CORRESPONDING COMPUTING DEVICE

CROSS-REFERENCE TO RELATED APPLICATIONS

This application is a national stage of Application No. PCT/NL2020/050089 filed Feb. 17, 2020 that claims the benefit of priority from Netherlands Application No. 2022598 filed on Feb. 19, 2019, which are both incorporated by reference in their entireties.

BACKGROUND

The present disclosure is directed to a method of performing an eye examination test. More specifically, the present disclosure is directed to an eye examination test using a computing device.

An eye examination test is, typically, a series of tests performed by a professional, for example an optician, an ophthalmologist or anything alike. An eye examination test may be used for testing the visual acuity, pupil function, extraocular muscle motility, ophthalmoscopy through an undilated pupil, amongst other things. The assessment of the refractive state of the eye may also be an important part of ophthalmic and optometric clinical practice. Such eye examination tests may also be used to detect potentially treatable blinding eye diseases, ocular manifestations of systemic disease, or signs of tumours or other anomalies of the brain.

Conventionally, a user needs to visit an optician, or ophthalmologist, to examine his/her eyes. Several tools may be required to examine the eyes of the user. The optician, or ophthalmologist, then performs some eye examination tests and adjusts the tests based on input he/she receives from the user. In the end, the optician, or ophthalmologist is able to provide a conclusion related to the eyes based on the tests that were performed.

In the last couple of years, online eye examination tests have been developed. As such, a user no longer needs to physically visit an optician, or ophthalmologist, but is able to perform the eye examination test online. The development of an unsupervised online subjective refraction method makes a refraction more accessible and may be quite cost-saving.

A known method of performing an eye examination test uses a computing device as well as a User Equipment. The computing device comprises a screen for displaying all kinds of eye examination test related visualizations. The User Equipment, for example a mobile phone, is used as an input tool. The user provides its input on questionnaires displayed on the screen using the User Equipment.

In order for the eye examination test to be performed accurately, it may be required that the user is placed in front of the screen at a distance of about three metres. The user is guided to this distance using the shoe size of the user. That is, the user needs to input his/her shoe size into the online eye examination test. Based on the inputted shoe size, the total amount of heel-toe steps are calculated. For example, for a shoe size 10, about 10 heel-toe steps are required to get to the above mentioned three metres distance. The user is then requested to perform 10 heel-toe steps to assure that the user is at about three metres distance from the screen.

One of the drawbacks of the known eye examination test as disclosed above is that the environment in which the eye examination test is to be performed is not controlled by a professional. The environment is, typically, the home of the user where the environment is created by the user. The environment may not be ideal to be used in an eye examination test.

SUMMARY

It is an object of the present disclosure to achieve an eye examination test for examining eyes of the user wherein the environment, i.e. the surroundings of a user, have minimum impact on the results of the test.

It is another object of the present disclosure to achieve a corresponding computing device for performing the eye examination test.

To better address one or more of the concerns of the prior art, in a first aspect of the disclosure, there is provided a method of performing an eye examination test for examining eyes of a user, said method using a computing device, said computing device comprising an image capturing unit arranged for capturing images.

The method comprising the steps of:
capturing, by said capturing unit, an image of said user and its surroundings;
dividing, by said computing device, said captured image into a plurality of bins, preferably a plurality of horizontal bins and a plurality of vertical bins;
estimating, by said computing device, light intensity of each of said plurality of bins, preferably each of said plurality of horizontal and vertical bins;
determining, by said computing device, an area of anomalous light intensity in said captured image based on said step of estimation wherein said estimated light intensity is above a predetermined threshold value;
performing, by said computing device, said eye examination test, taking said determined area of anomalous light into account.

It was one of the insights of the inventors that areas in the image that have anomalous light conditions should be taken into account during the eye examination test.

In the context of the present disclosure, an area having an anomalous light intensity may be defined as an area having a light intensity which substantially deviates from a standard, predefined, light intensity of from an average light intensity of the image itself.

In order to detect anomalous light in a particular area of the image, the image is first divided into a plurality of horizontal bins and a plurality of vertical bins. As such a grid of bins may be applied to the image, the grid consists of, for example, 8×8 bins, 16×16 bins, 64×64 bins, 128×128 bins, 256×256 bins or anything alike.

The resolution of the grid that is used, i.e. the amount of bins, may, for example, depend on the focal length of the lens that is used by the capturing unit when capturing the corresponding image. Another, or similar option, would be to derive the resolution from the actual size of detected eyes of the user in the image.

Once divided, the light intensity of each of the plurality of horizontal and vertical bins may be estimated. This may, for example, be performed by analysing Red-Green-Blue, RGB, values for the pixels in a particular bin. The RGB values may be translated to a measure of the light intensity using, for example, formula's like $0.2126*R+0.7152*G+0.0722*B$. The outcome is thus a measure for the brightness of a particular RGB pixel. All values within a particular bin may be averaged to obtain an average measure for the brightness of the particular bin.

Once the light intensities of each of the plurality of horizontal and vertical bins are estimated, it is determined whether a particular area in the image comprises anomalous light intensity. This is performed by comparing the estimated light intensities with a predetermined threshold value.

It is noted that the predetermined threshold value may be directed to a particular maximum brightness value and/or to a particular minimum brightness value. If one, or a plurality of estimated light intensities of adjacent bins exceed the predetermined threshold, it is determined that the associated area of those particular bins have an anomalous light intensity. The anomalous light intensity may, thus, be a light intensity which is considered too low, or too high.

Finally, the eye examination test is performed taking the determined area of anomalous light, more specifically the area which is considered to have anomalous light, into account.

In accordance with the present disclosure, the computing device may be any of a desktop computer, a tablet, a laptop, or anything alike. For example, such a computing device will run an internet browser which supports the eye examination test as disclosed.

Examples according to the present disclosure are described in the following.

In an example according to the first aspect of the present disclosure, the predetermined threshold value is based on an average light intensity of the captured image.

In a further example of the present disclosure, the predetermined threshold value is predefined and is configured in said computing device.

It is noted that the British standard of illuminance has recommended an illuminance of 500 lx during an eye examination test, both for general lighting and reading and colour vision tests with vision charts. Such a specific value may be used for determining the predetermined threshold value that is configured in the computing device. For example, if the averaged illuminance of a particular bin exceeds 1000 lx it may be considered that the light intensity of that particular bin is anomalous.

In a further example, the computing device is communicatively coupled to a display panel, wherein said step of performing said eye examination test comprises:
  indicating, by said computing device, via said display panel to said user, that said determined area of anomalous light exceeds said predetermined threshold value.

One of the advantages of the above described example is that the user may be instructed to take adequate action for improving the lighting situation. For example, the user may be requested to turn down specific (spot) lights, may be requested to increase the overall lighting in the room or anything alike.

In another example, the computing device is communicatively coupled to an audio device, wherein said step of performing said eye examination test comprises:
  indicating, by said computing device, via said audio device, to said user, that said determined area of anomalous light exceeds said predetermined threshold value.

The user may be instructed via a screen associated with the computing device, via a smart phone, tablet or anything alike.

In a further example, the step of performing said eye examination comprises the step of:
  estimating, by said computing device, an average light intensity of said captured image;
  determining, by said computing device, that said average light intensity is incompatible with a predefined average light intensity;
  requesting, by said computing device, said user to amend lighting in said surroundings of said user based on said determination.

The above described example describes the situation in which the environment lighting, for example the background lighting, does not suffice for performing the eye examination test. The background lighting may be too bright, or may be too dark. As mentioned above, preferably, the background lighting is somewhere between 400 lx-600 lx, or something similar. In case the determined average light intensity differs too much from the 400 lx-600 lx, the user may be requested to amend the lighting in the surroundings of the user accordingly.

Such a request may be conveyed to the user using a screen associated with the computing device, or may be conveyed using a particular mobile user device like a smart phone, a tablet or anything alike.

In an even further example, the method further comprises the steps of:
  detecting, by said computing device, locations of both eyes of said user in said captured image;
  determining, by said computing device, a perceived light intensity of each of said eyes separately, based on said step of estimating said light intensity of each of said plurality of horizontal and vertical bins and said detected locations;
  and wherein said step of performing comprises:
  performing, by said computing device, said eye examination test, taking into account said determined perceived light intensity of each of said eyes separately.

It was found that the light intensity perceived by a particular eye may also have an impact on the results of the eye examination test. The results may be improved by differentiating the light intensity perceived by each eye of the user. The eye examination test may then take into account that, for example, the light intensity perceived by the left eye differs from the light intensity perceived by the right eye.

The location of the eyes of the user in the captured image may be detected using particular face recognition algorithms. The eyes may be detected using anthropological characteristics of the face, for example, or may be detected using any other means available.

The average light intensity of each of the eyes may then be calculated. That is, the average light intensity of the locations corresponding to each of the eyes may be determined separately.

In a second aspect, there is provided a computing device for performing an eye examination test for examining eyes of a user, wherein said computing device comprises:
  an image capturing unit arranged for capturing an image of said user and its surroundings;
  a processing unit arranged for:
    dividing said captured image into a plurality of horizontal bins and a plurality of vertical bins;
    estimating light intensity of each of said plurality of horizontal and vertical bins;
    determining an area of anomalous light intensity in said captured image based on said estimation wherein said estimated light intensity is above a predetermined threshold value;
  and wherein said computing device is further arranged for performing said eye examination test taking said determined area of anomalous light into account.

It is hereby noted that the advantages and definitions of the first aspect of the present disclosure, being the method of performing an eye examination test for examining eyes of a user, are also associated with the second aspect of the present disclosure, being the computing device for performing an eye examination test for examining eyes of a user.

The computing device may be any type of device suitable for performing an eye examination test. Typically, it comprises a processing unit for processing all kinds of operations. It further comprises a screen for visualizing, to the user, all kinds of visualizations to which the user should provide his or her input. The present application is not directed to the specifics of the eye examination test that is to be performed.

The computing device is, for example, a laptop, tablet, a desktop or anything alike. The image capturing unit may be a webcam that is part of, i.e. an integral part of, the computing device. The webcam may also be, for example, a USB device that connects to a USB port.

In the above, an image capturing unit and a processing unit are explained. In accordance with the present disclosure, the image capturing unit may also be an image capturing device, an image capturing means, an image capturing module or anything alike. The processing unit may also be a processing device, a processing means a processing module or anything alike.

In an example, the predetermined threshold value is based on an average light intensity of said captured image.

In a further example, the predetermined threshold value is predefined and is configured in said computing device.

In another example, the computing device is communicatively coupled to a display panel, wherein said processing unit is further arranged for:
  indicating, via said display panel to said user, that said determined area of anomalous light exceeds said predetermined threshold value.

In a further example, the computing device is communicatively coupled to an audio device, wherein said processing unit is further arranged for:
  indicating, via said audio device to said user, that said determined area of anomalous light exceeds said predetermined threshold value.

In yet another example, the processing unit is further arranged for:
  estimating an average light intensity of said captured image;
  determining that said average light intensity is incompatible with a predefined average light intensity;
  requesting said user to amend lighting in said surroundings of said user based on said determination.

In a further example, the processing unit is further arranged for:
  detecting locations of both eyes of said user in said captured image;
  determining a perceived light intensity of each of said eyes separately based on said step of estimating said light intensity of each of said plurality of horizontal and vertical bins and said detected locations;
  and wherein said computing device is further arranged for performing said eye examination test taking into account said determined perceived light intensity of each of said eyes separately.

In a third aspect of the present disclosure, there is provided a computer program product comprising a computer readable medium having instruction stored thereon, which instruction, when executed by a computing device, cause said computing device to implement a method in accordance with any of the examples as provided above.

These and other aspects of the disclosure will be apparent from and elucidated with reference to the embodiments described hereinafter.

DETAILED DESCRIPTION

Figure 1:
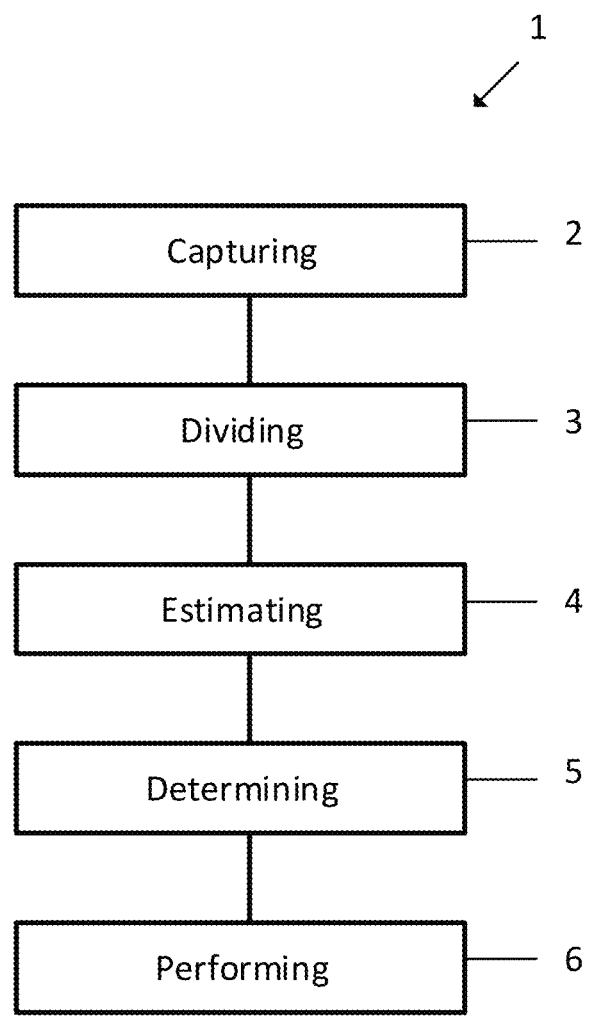
FIG. 1 schematically illustrates a method in accordance with the present disclosure.

FIG. 1 schematically illustrates a method 1 in accordance with the present disclosure.

A method of performing an eye examination test for examining eyes of a user, said method using a computing device, said computing device comprising an image capturing unit arranged for capturing images.

One of the aspects of the presented method is that the environmental lighting in the images taken from a particular user is analysed. In certain areas of the images anomalous light intensity may be determined. The eye examination test may then still be performed taken into account the areas in which the light intensity if anomalous. Alternatively, or in addition thereto, corrective measures may be performed for assuring that future captured images do not comprise areas of anomalous light intensity. For example, a user may be requested to move the capturing unit, to turn down the environmental lighting, to increase the environmental lighting, or anything alike.

In a first step, the method comprises the step of capturing, by said capturing unit, an image of said user and its surroundings.

The presented method is directed to the concept that a single image of the user and its surroundings are captured. It is however noted that multiple images of the user may be captured for increasing the reliability of the method.

In a next step, the method comprises the step of dividing said captured image into a plurality of horizontal bins and a plurality of vertical bins.

The image may, for example, be divided into a plurality of tiles, also referred to as bins. The presented method is not restricted to the amount of tiles, and also not to the shape of the tiles. Preferably, the same sized tiles are used such that each of the tiles are shaped equally. Even more preferably, the tiles are shaped rectangular for example squared.

In a next step, the light intensity of each of the plurality of tiles, for example horizontal and vertical bins, are estimated. Next, an area of anomalous light intensity in said captured image is determined based on said step of estimation wherein said estimated light intensity is above a predetermined threshold value. Finally, the eye examination test is performed taking said determined area of anomalous light into account.

Figure 2:
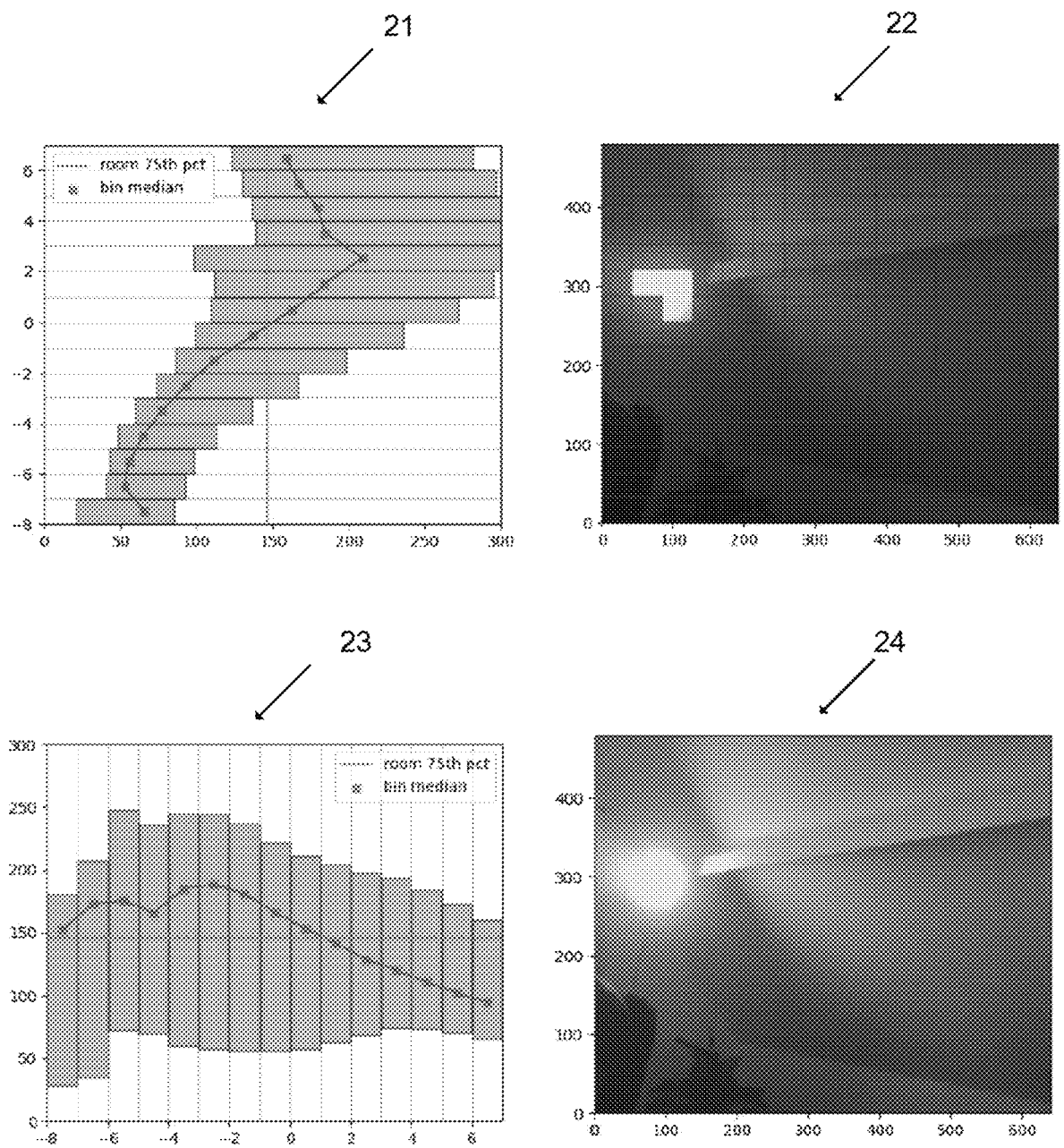
FIG. 2 schematically illustrates four images illustrating the process of determining that a background light source may have a negative effect on the results of the eye examination test.

FIG. 2 schematically illustrates four images 21, 22, 23, 24 illustrating the process of determining that a background light source may have a negative effect on the results of the eye examination test.

It is noted that, typically, a user starts a particular eye examination test when it is in front of a screen. The distance between the eyes of the user and the screen may be estimated to be roughly 65 cm. The image capturing unit may then capture images of the user at regular intervals.

In a first step, a calibration process may be performed, which may determine the focal length of the image capturing unit, more specifically of the lens of the image capturing unit, based on an average pupillary distance, i.e. the distance between the eyes of the user. During the calibration process, the user may sit substantially still in front of the screen.

The user may then be guided, or requested, to a certain distance from the screen, for example three meters. Preferably, the eye examination test is performed at about three meters from the screen to improve the results of the test. The distance may also be decreased in case the user is not able to recognize any symbols on the screen to about one or two meters.

As mentioned above, the recommended standard of illuminance during an eye examination test may be 500 lx for both general lighting and reading and colour vision tests with vision charts. First, the average illuminance of the room may be estimated, for example, by analysing each of the pixels of the captured image.

Next, the median illuminance along with its $25^{th}$ and $75^{th}$ percentile is computed over the frame of the captured image. If the measured illuminance is considered incompatible with the recommended 500 lx, the patient may be instructed either dim or brighten the light accordingly. Alternatively, or in addition to, the eye examination test may take into account any anomalies in the light distribution.

The horizontal and vertical distribution of illuminance may then be calculated over a grid of n^2 bins. To detect anomalies in the background light distribution, the algorithm may calculate the median illuminance, along with the $25^{th}$ and $75^{th}$ percentile. An anomalous source of light may be detected where the difference between the bin's median illuminance and the environment's $75^{th}$ percentile may be larger than a threshold value. The threshold value may vary as a function of the grid resolution and the environment's illuminance variance.

Examples of the above is shown in FIG. 2. Reference numeral 21 indicates a graph in which the binned illuminance is shown. Horizontally is plotted the binned illuminance and vertically is plotted the amount of bins from the centre. Reference numeral 22 shows a processed image in which a particular light source is illustrated, wherein horizontally is plotted a measure related to the horizontal distance and wherein vertically is plotted a measure related to the vertical distance. Reference numeral 24 shows the original captured image and reference numeral 23 shows a graph in which the binned illuminance is shown. Horizontally is plotted the bins from the centre and vertically is plotted the binned illuminance.

Figure 3:
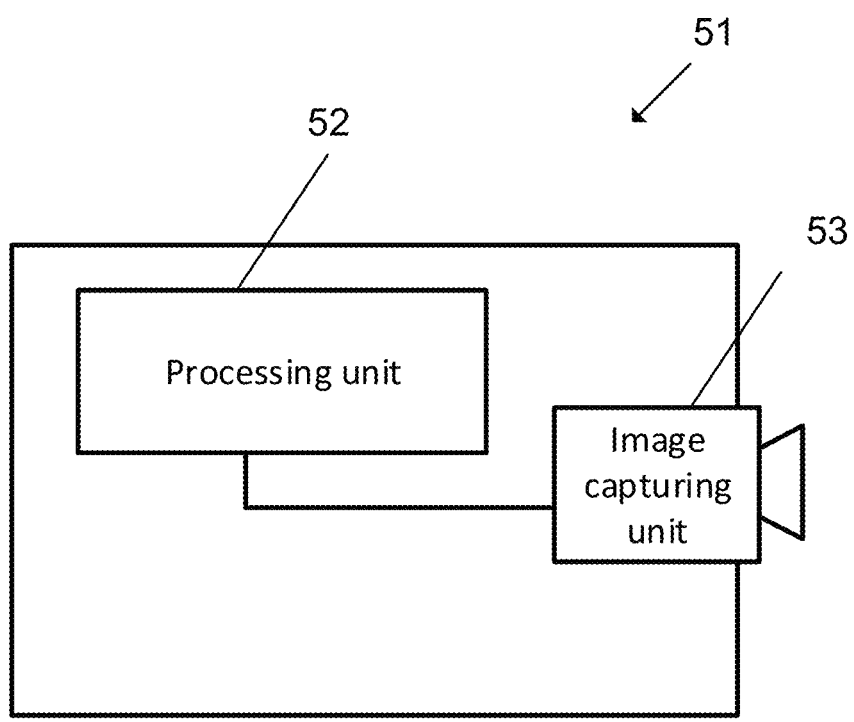
FIG. 3 schematically illustrates a computing device in accordance with the present disclosure.

FIG. 3 shows a computing device 51 for performing an eye examination test for examining eyes of a user, wherein said computing device comprises:
an image capturing unit 53 arranged for capturing an image of said user and its surroundings;
a processing unit 52 arranged for:
dividing said captured image into a plurality of horizontal bins and a plurality of vertical bins;
estimating light intensity of each of said plurality of horizontal and vertical bins;
determining an area of anomalous light intensity in said captured image based on said estimation wherein said estimated light intensity is above a predetermined threshold value;
and wherein said computing device is further arranged for performing said eye examination test taking said determined area of anomalous light into account.

The present disclosure is not limited to the examples as disclosed above, and can be modified and enhanced by those skilled in the art beyond the scope of the present disclosure as disclosed in the appended claims without having to apply inventive skills.

The invention claimed is:

1. A method of performing an eye examination test for examining eyes of a user, said method using a computing device, said computing device comprising an image capturing unit arranged for capturing images, said method comprising the steps of:
capturing, by said capturing unit, an image of said user and its surroundings;
dividing, by said computing device, said captured image into a plurality bins;
estimating, by said computing device, light intensity of each of said bins;
determining, by said computing device, an area of anomalous light intensity in said captured image based on said step of estimation wherein said estimated light intensity is above a predetermined threshold value;
performing, by said computing device, said eye examination test, taking said determined area of anomalous light into account.

2. The method according to claim 1, wherein said predetermined threshold value is based on an average light intensity of said captured image.

3. The method according to claim 1, wherein said predetermined threshold value is predefined and is configured in said computing device.

4. The method according to claim 1, wherein said computing device is communicatively coupled to a display panel, wherein said step of performing said eye examination test comprises:
indicating, by said computing device, via said display panel to said user, that said determined area of anomalous light exceeds said predetermined threshold value.

5. The method according to claim 1, wherein said computing device is communicatively coupled to an audio device, wherein said method further comprises the step of:
indicating, by said computing device, via said audio device, to said user, that said determined area of anomalous light exceeds said predetermined threshold value.

6. The method according to claim 1, wherein said step of performing said eye examination comprises the step of:
estimating, by said computing device, an average light intensity of said captured image;
determining, by said computing device, that said average light intensity is incompatible with a predefined average light intensity;
requesting, by said computing device, said user to amend lighting in said surroundings of said user based on said determination.

7. The method according to claim 1, wherein said method further comprises the steps of:
detecting, by said computing device, locations of both eyes of said user in said captured image;
determining, by said computing device, a perceived light intensity of each of said eyes separately, based on said step of estimating said light intensity of each of said plurality of bins and said detected locations;
and wherein said step of performing comprises:

performing, by said computing device, said eye examination test, taking into account said determined perceived light intensity of each of said eyes separately.

8. A computing device for performing an eye examination test for examining eyes of a user, wherein said computing device comprises:
   an image capturing unit arranged for capturing an image of said user and its surroundings;
   a processing unit arranged for:
      dividing said captured image into a plurality bins;
      estimating light intensity of each of said plurality of bins;
      determining an area of anomalous light intensity in said captured image based on said estimation wherein said estimated light intensity is above a predetermined threshold value;
      and wherein said computing device is further arranged for performing said eye examination test taking said determined area of anomalous light into account.

9. The computing device in accordance with claim 8, wherein said predetermined threshold value is based on an average light intensity of said captured image.

10. The computing device in accordance with claim 8, wherein said predetermined threshold value is predefined and is configured in said computing device.

11. The computing device in accordance with claim 8, wherein said computing device is communicatively coupled to a display panel, wherein said processing unit is further arranged for:
   indicating, via said display panel to said user, that said determined area of anomalous light exceeds said predetermined threshold value.

12. The computing device in accordance with claim 8, wherein said computing device is communicatively coupled to an audio device, wherein said processing unit is further arranged for:
   indicating, via said audio device, to said user, that said determined area of anomalous light exceeds said predetermined threshold value.

13. The computing device in accordance with claim 8, wherein said processing unit is further arranged for:
   estimating an average light intensity of said captured image;
   determining that said average light intensity is incompatible with a predefined average light intensity;
   requesting said user to amend lighting in said surroundings of said user based on said determination.

14. The computing device in accordance with claim 8, wherein said processing unit is further arranged for:
   detecting locations of both eyes of said user in said captured image;
   determining a perceived light intensity of each of said eyes separately based on said step of estimating said light intensity of each of said plurality of bins and said detected locations;
   and wherein said computing device is further arranged for performing said eye examination test taking into account said determined perceived light intensity of each of said eyes separately.

\* \* \* \* \*